United States Patent
Chowaniec et al.

(10) Patent No.: US 10,292,705 B2
(45) Date of Patent: May 21, 2019

(54) SURGICAL APPARATUS

(71) Applicant: Covidien LP, Mansfield, MA (US)

(72) Inventors: David Chowaniec, Rocky Hill, CT (US); Pawel Abramek, Berlin, CT (US); David Fowler, Cheshire, CT (US); Matthew D'errico, Middletown, CT (US)

(73) Assignee: Covidien LP, Mansfield, MA (US)

( * ) Notice: Subject to any disclaimer, the term of this patent is extended or adjusted under 35 U.S.C. 154(b) by 337 days.

(21) Appl. No.: 15/292,463

(22) Filed: Oct. 13, 2016

(65) Prior Publication Data

US 2017/0128067 A1 May 11, 2017

Related U.S. Application Data

(60) Provisional application No. 62/251,737, filed on Nov. 6, 2015.

(51) Int. Cl.
*A61B 17/072* (2006.01)
*A61B 17/068* (2006.01)
(Continued)

(52) U.S. Cl.
CPC ...... *A61B 17/072* (2013.01); *A61B 17/07207* (2013.01); *A61B 17/068* (2013.01);
(Continued)

(58) Field of Classification Search
CPC .......... A61B 17/068; A61B 17/072; A61B 17/07207; A61B 17/115;
(Continued)

(56) References Cited

U.S. PATENT DOCUMENTS 2,777,340 A   1/1957   Hettwer et al.
2,957,353 A   10/1960  Babacz
(Continued)

FOREIGN PATENT DOCUMENTS

CA   2451558 A1   1/2003
CN   1547454 A    11/2004
(Continued)

OTHER PUBLICATIONS

Extended European Search Report corresponding to counterpart International Application No. EP 14 18 4882.0 dated May 12, 2015.
(Continued)

*Primary Examiner* — Scott A Smith

(57) ABSTRACT

A surgical apparatus includes a handle, an elongate member and a switch actuator. The switch actuator includes an activation link and a switch plunger coupled to the activation link. An electric switch is mounted to the elongate member. A rotatable lock member is mounted to the elongate member and adapted for rotational movement between an unlocked condition and a locked condition. The rotatable lock member includes an actuator stop dimensioned to operatively engage the switch actuator to prevent movement of the switch actuator from a first longitudinal position to a second longitudinal position when in the unlocked condition, and to permit movement of the switch actuator to the second longitudinal position when rotated to the locked condition such that the switch plunger activates the switch. A loading unit is releasably couplable to the rotatable lock member and is secured relative to the elongate member when the rotatable lock member is in the locked condition.

16 Claims, 7 Drawing Sheets

(51) Int. Cl.
  *A61B 17/00* (2006.01)
  *A61B 90/00* (2016.01)
  *A61B 90/98* (2016.01)
(52) U.S. Cl.
  CPC ..... *A61B 90/98* (2016.02); *A61B 2017/00017* (2013.01); *A61B 2017/00398* (2013.01); *A61B 2017/00464* (2013.01); *A61B 2017/00473* (2013.01); *A61B 2017/00734* (2013.01); *A61B 2017/07271* (2013.01); *A61B 2090/0808* (2016.02); *A61B 2090/0811* (2016.02)
(58) Field of Classification Search
  CPC ........... A61B 2017/00398; A61B 2017/00473; A61B 2017/00017; A61B 2017/00464; A61B 2017/00734; A61B 2017/07214; A61B 17/00234; A61B 2090/0808; A61B 2090/0811
  USPC .............. 227/19, 175.1, 175.2, 176.1, 180.1; 606/75, 139, 153, 219
  See application file for complete search history.

(56) References Cited

U.S. PATENT DOCUMENTS

| | | | |
|---|---|---|---|
| 3,111,328 | A | 11/1963 | Di Rito et al. |
| 3,695,058 | A | 10/1972 | Keith, Jr. |
| 3,734,515 | A | 5/1973 | Dudek |
| 3,759,336 | A | 9/1973 | Marcovitz et al. |
| 4,162,399 | A | 7/1979 | Hudson |
| 4,606,343 | A | 8/1986 | Conta et al. |
| 4,705,038 | A | 11/1987 | Sjostrom et al. |
| 4,722,685 | A | 2/1988 | de Estrada et al. |
| 4,823,807 | A | 4/1989 | Russell et al. |
| 4,874,181 | A | 10/1989 | Hsu |
| 5,129,118 | A | 7/1992 | Walmesley |
| 5,129,570 | A | 7/1992 | Schulze et al. |
| 5,152,744 | A | 10/1992 | Krause et al. |
| 5,301,061 | A | 4/1994 | Nakada et al. |
| 5,312,023 | A | 5/1994 | Green et al. |
| 5,326,013 | A | 7/1994 | Green et al. |
| 5,350,355 | A | 9/1994 | Sklar |
| 5,383,874 | A | 1/1995 | Jackson et al. |
| 5,383,880 | A | 1/1995 | Hooven |
| 5,389,098 | A | 2/1995 | Tsuruta et al. |
| 5,395,033 | A | 3/1995 | Byrne et al. |
| 5,400,267 | A | 3/1995 | Denen et al. |
| 5,411,508 | A | 5/1995 | Bessler et al. |
| 5,413,267 | A | 5/1995 | Solyntjes et al. |
| 5,427,087 | A | 6/1995 | Ito et al. |
| 5,433,721 | A | 7/1995 | Hooven et al. |
| 5,467,911 | A | 11/1995 | Tsuruta et al. |
| 5,476,379 | A | 12/1995 | Disel |
| 5,487,499 | A | 1/1996 | Sorrentino et al. |
| 5,518,163 | A | 5/1996 | Hooven |
| 5,518,164 | A | 5/1996 | Hooven |
| 5,526,822 | A | 6/1996 | Burbank et al. |
| 5,529,235 | A | 6/1996 | Boiarski et al. |
| 5,535,934 | A | 7/1996 | Boiarski et al. |
| 5,535,937 | A | 7/1996 | Boiarski et al. |
| 5,540,375 | A | 7/1996 | Bolanos et al. |
| 5,540,706 | A | 7/1996 | Aust et al. |
| 5,542,594 | A | 8/1996 | McKean et al. |
| 5,549,637 | A | 8/1996 | Crainich |
| 5,553,675 | A | 9/1996 | Pitzen et al. |
| 5,562,239 | A | 10/1996 | Boiarski et al. |
| 5,564,615 | A | 10/1996 | Bishop et al. |
| 5,609,560 | A | 3/1997 | Ichikawa et al. |
| 5,626,587 | A | 5/1997 | Bishop et al. |
| 5,632,432 | A | 5/1997 | Schulze et al. |
| 5,645,209 | A | 7/1997 | Green et al. |
| 5,647,526 | A | 7/1997 | Green et al. |
| 5,653,374 | A | 8/1997 | Young et al. |
| 5,658,300 | A | 8/1997 | Bito et al. |
| 5,662,662 | A | 9/1997 | Bishop et al. |
| 5,667,517 | A | 9/1997 | Hooven |
| 5,693,042 | A | 12/1997 | Boiarski et al. |
| 5,704,534 | A | 1/1998 | Huitema et al. |
| 5,713,505 | A | 2/1998 | Huitema |
| 5,762,603 | A | 6/1998 | Thompson |
| 5,779,130 | A | 7/1998 | Alesi et al. |
| 5,782,396 | A | 7/1998 | Mastri et al. |
| 5,782,397 | A | 7/1998 | Koukline |
| 5,792,573 | A | 8/1998 | Pitzen et al. |
| 5,797,536 | A | 8/1998 | Smith et al. |
| 5,820,009 | A | 10/1998 | Melling et al. |
| 5,863,159 | A | 1/1999 | Lasko |
| 5,908,427 | A | 6/1999 | McKean et al. |
| 5,954,259 | A | 9/1999 | Viola et al. |
| 5,964,774 | A | 10/1999 | McKean et al. |
| 5,993,454 | A | 11/1999 | Longo |
| 6,010,054 | A | 1/2000 | Johnson et al. |
| 6,017,354 | A | 1/2000 | Culp et al. |
| 6,032,849 | A | 3/2000 | Mastri et al. |
| 6,045,560 | A | 4/2000 | McKean et al. |
| 6,090,123 | A | 7/2000 | Culp et al. |
| 6,126,651 | A | 10/2000 | Mayer |
| 6,129,547 | A | 10/2000 | Cise et al. |
| 6,165,169 | A | 12/2000 | Panescu et al. |
| 6,239,732 | B1 | 5/2001 | Cusey |
| 6,241,139 | B1 | 6/2001 | Milliman et al. |
| 6,264,086 | B1 | 7/2001 | McGuckin, Jr. |
| 6,264,087 | B1 | 7/2001 | Whitman |
| 6,302,311 | B1 | 10/2001 | Adams et al. |
| 6,315,184 | B1 | 11/2001 | Whitman |
| 6,321,855 | B1 | 11/2001 | Barnes |
| 6,329,778 | B1 | 12/2001 | Culp et al. |
| 6,343,731 | B1 | 2/2002 | Adams et al. |
| 6,348,061 | B1 | 2/2002 | Whitman |
| 6,368,324 | B1 | 4/2002 | Dinger et al. |
| 6,371,909 | B1 | 4/2002 | Hoeg et al. |
| 6,434,507 | B1 | 8/2002 | Clayton et al. |
| 6,443,973 | B1 | 9/2002 | Whitman |
| 6,461,372 | B1 | 10/2002 | Jensen et al. |
| 6,488,197 | B1 | 12/2002 | Whitman |
| 6,491,201 | B1 | 12/2002 | Whitman |
| 6,533,157 | B1 | 3/2003 | Whitman |
| 6,537,280 | B2 | 3/2003 | Dinger et al. |
| 6,610,066 | B2 | 8/2003 | Dinger et al. |
| 6,611,793 | B1 | 8/2003 | Burnside et al. |
| 6,645,218 | B1 | 11/2003 | Cassidy et al. |
| 6,654,999 | B2 | 12/2003 | Stoddard et al. |
| 6,698,643 | B2 | 3/2004 | Whitman |
| 6,699,177 | B1 | 3/2004 | Wang et al. |
| 6,716,233 | B1 | 4/2004 | Whitman |
| 6,743,240 | B2 | 6/2004 | Smith et al. |
| 6,783,533 | B2 | 8/2004 | Green et al. |
| 6,792,390 | B1 | 9/2004 | Burnside et al. |
| 6,793,652 | B1 | 9/2004 | Whitman et al. |
| 6,817,508 | B1 | 11/2004 | Racenet et al. |
| 6,830,174 | B2 | 12/2004 | Hillstead et al. |
| 6,846,308 | B2 | 1/2005 | Whitman et al. |
| 6,846,309 | B2 | 1/2005 | Whitman et al. |
| 6,849,071 | B2 | 2/2005 | Whitman et al. |
| 6,860,892 | B1 | 3/2005 | Tanaka et al. |
| 6,899,538 | B2 | 5/2005 | Matoba |
| 6,905,057 | B2 | 6/2005 | Swayze et al. |
| 6,959,852 | B2 | 11/2005 | Shelton, IV et al. |
| 6,964,363 | B2 | 11/2005 | Wales et al. |
| 6,981,628 | B2 | 1/2006 | Wales |
| 6,981,941 | B2 | 1/2006 | Whitman et al. |
| 6,986,451 | B1 | 1/2006 | Mastri et al. |
| 6,988,649 | B2 | 1/2006 | Shelton, IV et al. |
| 7,032,798 | B2 | 4/2006 | Whitman et al. |
| RE39,152 | E | 6/2006 | Aust et al. |
| 7,055,731 | B2 | 6/2006 | Shelton, IV et al. |
| 7,059,508 | B2 | 6/2006 | Shelton, IV et al. |
| 7,077,856 | B2 | 7/2006 | Whitman |
| 7,111,769 | B2 | 9/2006 | Wales et al. |
| 7,122,029 | B2 | 10/2006 | Koop et al. |
| 7,140,528 | B2 | 11/2006 | Shelton, IV |
| 7,141,049 | B2 | 11/2006 | Stern et al. |
| 7,143,923 | B2 | 12/2006 | Shelton, IV et al. |

(56) References Cited

U.S. PATENT DOCUMENTS

| | | | |
|---|---|---|---|
| 7,143,925 | B2 | 12/2006 | Shelton, IV et al. |
| 7,143,926 | B2 | 12/2006 | Shelton, IV et al. |
| 7,147,138 | B2 | 12/2006 | Shelton, IV |
| 7,172,104 | B2 | 2/2007 | Scirica et al. |
| 7,225,964 | B2 | 6/2007 | Mastri et al. |
| 7,238,021 | B1 | 7/2007 | Johnson |
| 7,246,734 | B2 | 7/2007 | Shelton, IV |
| 7,252,660 | B2 | 8/2007 | Kunz |
| 7,328,828 | B2 | 2/2008 | Ortiz et al. |
| 7,364,061 | B2 | 4/2008 | Swayze et al. |
| 7,380,695 | B2 | 6/2008 | Doll et al. |
| 7,380,696 | B2 | 6/2008 | Shelton, IV et al. |
| 7,404,508 | B2 | 7/2008 | Smith et al. |
| 7,407,078 | B2 | 8/2008 | Shelton, IV et al. |
| 7,416,101 | B2 | 8/2008 | Shelton, IV et al. |
| 7,419,080 | B2 | 9/2008 | Smith et al. |
| 7,422,139 | B2 | 9/2008 | Shelton, IV et al. |
| 7,431,189 | B2 | 10/2008 | Shelton, IV et al. |
| 7,441,684 | B2 | 10/2008 | Shelton, IV et al. |
| 7,448,525 | B2 | 11/2008 | Shelton, IV et al. |
| 7,464,846 | B2 | 12/2008 | Shelton, IV et al. |
| 7,464,847 | B2 | 12/2008 | Viola et al. |
| 7,464,849 | B2 | 12/2008 | Shelton, IV et al. |
| 7,481,347 | B2 | 1/2009 | Roy |
| 7,481,824 | B2 | 1/2009 | Boudreaux et al. |
| 7,487,899 | B2 | 2/2009 | Shelton, IV et al. |
| 7,549,564 | B2 | 6/2009 | Boudreaux |
| 7,565,993 | B2 | 7/2009 | Milliman et al. |
| 7,568,603 | B2 | 8/2009 | Shelton, IV et al. |
| 7,575,144 | B2 | 8/2009 | Ortiz et al. |
| 7,588,175 | B2 | 9/2009 | Timm et al. |
| 7,588,176 | B2 | 9/2009 | Timm et al. |
| 7,637,409 | B2 | 12/2009 | Marczyk |
| 7,641,093 | B2 | 1/2010 | Doll et al. |
| 7,644,848 | B2 | 1/2010 | Swayze et al. |
| 7,670,334 | B2 | 3/2010 | Hueil et al. |
| 7,673,780 | B2 | 3/2010 | Shelton, IV et al. |
| 7,699,835 | B2 | 4/2010 | Lee et al. |
| 7,721,931 | B2 | 5/2010 | Shelton, IV et al. |
| 7,738,971 | B2 | 6/2010 | Swayze et al. |
| 7,740,159 | B2 | 6/2010 | Shelton, IV et al. |
| 7,743,960 | B2 | 6/2010 | Whitman et al. |
| 7,758,613 | B2 | 7/2010 | Whitman |
| 7,766,210 | B2 | 8/2010 | Shelton, IV et al. |
| 7,770,773 | B2 | 8/2010 | Whitman et al. |
| 7,770,775 | B2 | 8/2010 | Shelton, IV et al. |
| 7,793,812 | B2 | 9/2010 | Moore et al. |
| 7,799,039 | B2 | 9/2010 | Shelton, IV et al. |
| 7,802,712 | B2 | 9/2010 | Milliman et al. |
| 7,803,151 | B2 | 9/2010 | Whitman |
| 7,822,458 | B2 | 10/2010 | Webster, III et al. |
| 7,845,534 | B2 | 12/2010 | Viola et al. |
| 7,845,537 | B2 | 12/2010 | Shelton, IV et al. |
| 7,857,185 | B2 | 12/2010 | Swayze et al. |
| 7,870,989 | B2 | 1/2011 | Viola et al. |
| 7,887,530 | B2 * | 2/2011 | Zemlok .......... A61B 17/068 606/1 |
| 7,900,805 | B2 | 3/2011 | Shelton, IV et al. |
| 7,905,897 | B2 | 3/2011 | Whitman et al. |
| 7,918,230 | B2 | 4/2011 | Whitman et al. |
| 7,922,061 | B2 | 4/2011 | Shelton, IV et al. |
| 7,922,719 | B2 | 4/2011 | Ralph et al. |
| 7,947,034 | B2 | 5/2011 | Whitman |
| 7,951,071 | B2 | 5/2011 | Whitman et al. |
| 7,954,682 | B2 | 6/2011 | Giordano et al. |
| 7,959,051 | B2 | 6/2011 | Smith et al. |
| 7,963,433 | B2 | 6/2011 | Whitman et al. |
| 7,967,178 | B2 | 6/2011 | Scirica et al. |
| 7,967,179 | B2 | 6/2011 | Olson et al. |
| 7,992,758 | B2 | 8/2011 | Whitman et al. |
| 8,011,550 | B2 | 9/2011 | Aranyi et al. |
| 8,016,178 | B2 | 9/2011 | Olson et al. |
| 8,016,855 | B2 | 9/2011 | Whitman et al. |
| 8,020,743 | B2 | 9/2011 | Shelton, IV |
| 8,025,199 | B2 | 9/2011 | Whitman et al. |
| 8,035,487 | B2 | 10/2011 | Malackowski |
| 8,052,024 | B2 | 11/2011 | Viola et al. |
| 8,114,118 | B2 | 2/2012 | Knodel et al. |
| 8,127,975 | B2 | 3/2012 | Olson et al. |
| 8,132,705 | B2 | 3/2012 | Viola et al. |
| 8,152,516 | B2 | 4/2012 | Harvey et al. |
| 8,157,150 | B2 | 4/2012 | Viola et al. |
| 8,157,151 | B2 | 4/2012 | Ingmanson et al. |
| 8,182,494 | B1 | 5/2012 | Yencho et al. |
| 8,186,555 | B2 | 5/2012 | Shelton, IV et al. |
| 8,186,587 | B2 | 5/2012 | Zmood et al. |
| 8,220,367 | B2 | 7/2012 | Hsu |
| 8,235,273 | B2 | 8/2012 | Olson et al. |
| 8,241,322 | B2 | 8/2012 | Whitman et al. |
| 8,272,554 | B2 | 9/2012 | Whitman et al. |
| 8,292,150 | B2 | 10/2012 | Bryant |
| 8,292,888 | B2 | 10/2012 | Whitman |
| 8,342,379 | B2 | 1/2013 | Whitman et al. |
| 8,348,130 | B2 | 1/2013 | Shah et al. |
| 8,348,855 | B2 | 1/2013 | Hillely et al. |
| 8,353,440 | B2 | 1/2013 | Whitman et al. |
| 8,357,144 | B2 | 1/2013 | Whitman et al. |
| 8,365,633 | B2 | 2/2013 | Simaan et al. |
| 8,365,972 | B2 | 2/2013 | Aranyi et al. |
| 8,371,492 | B2 | 2/2013 | Aranyi et al. |
| 8,372,057 | B2 | 2/2013 | Cude et al. |
| 8,391,957 | B2 | 3/2013 | Carlson et al. |
| 8,397,971 | B2 * | 3/2013 | Yates .......... A61B 17/07207 227/175.1 |
| 8,403,926 | B2 | 3/2013 | Nobis et al. |
| 8,418,904 | B2 | 4/2013 | Wenchell et al. |
| 8,424,739 | B2 | 4/2013 | Racenet et al. |
| 8,454,585 | B2 | 6/2013 | Whitman |
| 8,505,802 | B2 | 8/2013 | Viola et al. |
| 8,517,241 | B2 | 8/2013 | Nicholas et al. |
| 8,523,043 | B2 | 9/2013 | Ullrich et al. |
| 8,551,076 | B2 | 10/2013 | Duval et al. |
| 8,561,871 | B2 | 10/2013 | Rajappa et al. |
| 8,561,874 | B2 | 10/2013 | Scirica |
| 8,602,287 | B2 | 12/2013 | Yates et al. |
| 8,623,000 | B2 | 1/2014 | Humayun et al. |
| 8,627,995 | B2 | 1/2014 | Smith et al. |
| 8,632,463 | B2 | 1/2014 | Drinan et al. |
| 8,636,766 | B2 | 1/2014 | Milliman et al. |
| 8,647,258 | B2 | 2/2014 | Aranyi et al. |
| 8,652,121 | B2 | 2/2014 | Quick et al. |
| 8,657,174 | B2 | 2/2014 | Yates et al. |
| 8,657,177 | B2 | 2/2014 | Scirica et al. |
| 8,672,206 | B2 | 3/2014 | Aranyi et al. |
| 8,696,552 | B2 | 4/2014 | Whitman |
| 8,708,213 | B2 | 4/2014 | Shelton, IV et al. |
| 8,715,306 | B2 | 5/2014 | Faller et al. |
| 8,758,391 | B2 | 6/2014 | Swayze et al. |
| 8,806,973 | B2 | 8/2014 | Ross et al. |
| 8,808,311 | B2 | 8/2014 | Heinrich et al. |
| 8,820,605 | B2 | 9/2014 | Shelton, IV |
| 8,851,355 | B2 | 10/2014 | Aranyi et al. |
| 8,858,571 | B2 | 10/2014 | Shelton, IV et al. |
| 8,875,972 | B2 | 11/2014 | Weisenburgh, II et al. |
| 8,888,762 | B2 | 11/2014 | Whitman |
| 8,893,946 | B2 | 11/2014 | Boudreaux et al. |
| 8,899,462 | B2 | 12/2014 | Kostrzewski et al. |
| 8,905,289 | B2 | 12/2014 | Patel et al. |
| 8,919,630 | B2 | 12/2014 | Milliman |
| 8,931,680 | B2 | 1/2015 | Milliman |
| 8,939,344 | B2 | 1/2015 | Olson et al. |
| 8,950,646 | B2 | 2/2015 | Viola |
| 8,960,519 | B2 | 2/2015 | Whitman et al. |
| 8,961,396 | B2 | 2/2015 | Azarbarzin et al. |
| 8,967,443 | B2 | 3/2015 | McCuen |
| 8,968,276 | B2 | 3/2015 | Zemlok et al. |
| 8,968,337 | B2 | 3/2015 | Whitfield et al. |
| 8,992,422 | B2 | 3/2015 | Spivey et al. |
| 9,016,545 | B2 | 4/2015 | Aranyi et al. |
| 9,023,014 | B2 | 5/2015 | Chowaniec et al. |
| 9,033,868 | B2 | 5/2015 | Whitman et al. |
| 9,055,943 | B2 | 6/2015 | Zemlok et al. |
| 9,064,653 | B2 | 6/2015 | Prest et al. |
| 9,072,515 | B2 | 7/2015 | Hall et al. |

(56) References Cited

U.S. PATENT DOCUMENTS

| | | |
|---|---|---|
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,706,674 B2 * | 7/2017 | Collins .................. H05K 7/06 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0216525 A1 | 8/2015 | Collins et al. |
| 2015/0272577 A1 | 10/2015 | Zemlok et al. |
| 2015/0297199 A1 | 10/2015 | Nicholas et al. |

(56) References Cited

U.S. PATENT DOCUMENTS

| | | |
|---|---|---|
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 1957854 A | 5/2007 |
| CN | 101495046 A | 7/2009 |
| CN | 102247182 A | 11/2011 |
| DE | 102008053842 A1 | 5/2010 |
| EP | 0705571 A1 | 4/1996 |
| EP | 1563793 A1 | 8/2005 |
| EP | 1769754 A1 | 4/2007 |
| EP | 2316345 A1 | 5/2011 |
| EP | 2668910 A2 | 12/2013 |
| ES | 2333509 A1 | 2/2010 |
| JP | 2005-125075 A | 5/2005 |
| KR | 20120022521 A | 3/2012 |
| WO | 2011/108840 A2 | 9/2011 |
| WO | 2012/040984 A1 | 4/2012 |

OTHER PUBLICATIONS

Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
Australian Examination Report No. 1 corresponding to International Application No. AU 2013205872 dated Oct. 19, 2016.
Australian Examination Report from Appl. No. AU 2013205840 dated Nov. 3, 2016.
European Search Report corresponding to EP 15 184 915.5-1654 dated Sep. 16, 2016.
Partial European Search Report in corresponding Application No. EP16197391, dated Apr. 4, 2017, 9 pages.

* cited by examiner

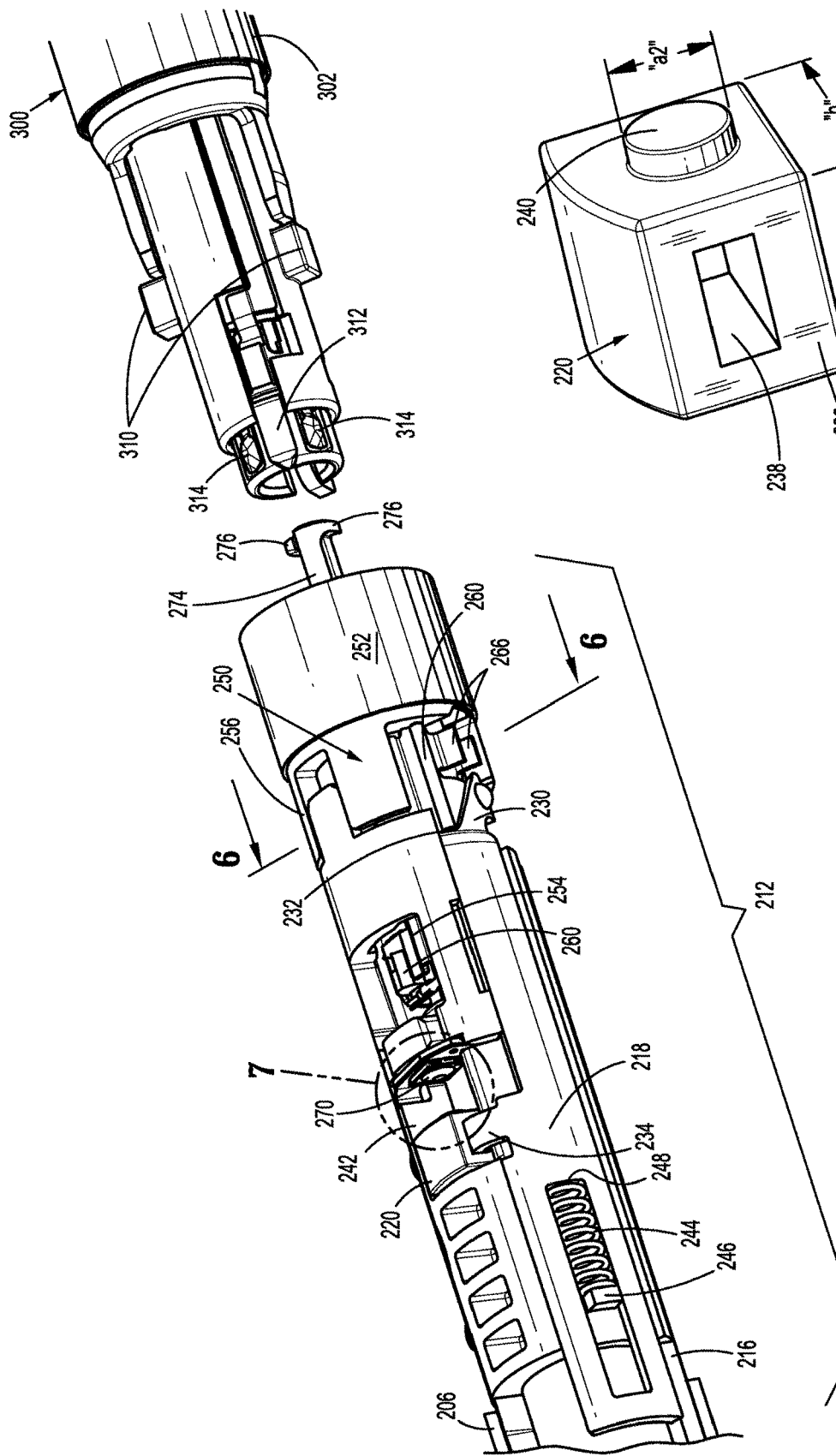

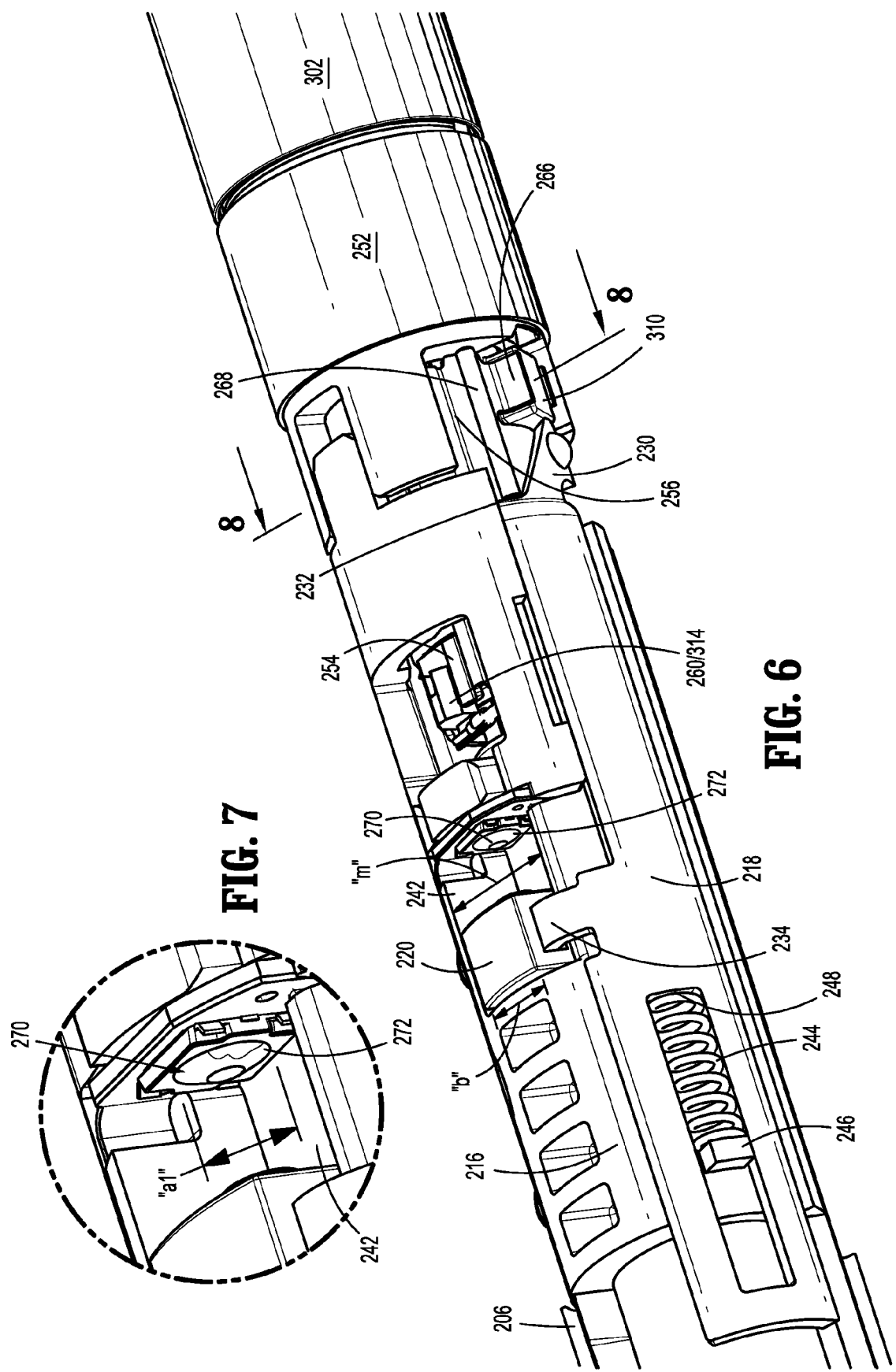

SURGICAL APPARATUS

CROSS-REFERENCE TO RELATED APPLICATIONS

This application claims the benefit of and priority to U.S. Provisional Patent Application No. 62/251,737, filed Nov. 6, 2015, the entire disclosure of which is incorporated by reference herein.

BACKGROUND

1. Technical Field

The present disclosure relates to a surgical fastener apparatus including a handle assembly and a disposable loading unit mountable relative to the handle assembly. More particularly, the present disclosure relates to a fastener apparatus having an activation mechanism to confirm and facilitate proper sequential mounting of multiple loading units relative to the handle assembly.

2. Background of Related Art

Surgical fastener apparatuses for applying fasteners or staples to tissue are well known. These fastener apparatuses include single use devices which are preloaded with one or more staples and are disposable after a single use. Multiple use devices are also available and are preloaded with a plurality of staples. Multiple use devices are disposable after the supply of staples has been exhausted or a surgical procedure has been completed. If the supply of staples is exhausted prior to completion of a surgical procedure, a new device may be required to complete the surgical procedure. The use of additional devices for a single surgical procedure can be expensive.

Covidien, LP, has manufactured and marketed stapling systems having replaceable cartridges, such as the Multifire ENDO GIA™ 30 and Multifire ENDO GIA™ 60 systems, for a number of years. These systems include an electromechanical handle assembly and a surgical loading unit. The loading unit may be a single use loading unit (SULU) or a multiple use loading unit (MULU). The loading unit includes a body and an end effector, and is attached to the handle assembly, and/or an adapter assembly associated with the handle assembly, immediately prior to surgery. The end effector may include a cartridge which houses a plurality of staples. After use, the loading unit can be removed relative to the adapter assembly and replaced with a new loading unit to perform additional stapling and/or cutting operations. A drive assembly is supported within the loading unit and is engagable with an associated drive mechanism of the adapter assembly to control operation of the loading unit.

Although these systems have provided significant clinical benefits, improvements are still possible. For example, since the handle and adapter assemblies are reusable it would be desirable to incorporate a mechanism which facilitates proper and repetitive coupling of the loading units to the adapter assembly without degradation of the mechanical or electrical operating components.

SUMMARY

Accordingly, the present disclosure is directed to a surgical apparatus including a handle, an elongate member coupled to the handle and defining a longitudinal axis, and a switch actuator mounted to the elongate member, and being adapted for longitudinal movement relative to the elongate member between first and second longitudinal positions. The switch actuator includes an activation link and a switch plunger coupled to the activation link. An electric switch is mounted to the elongate member in longitudinal alignment with the switch plunger. A rotatable lock member is mounted to the elongate member and adapted for rotational movement about the longitudinal axis between an unlocked condition and a locked condition. The rotatable lock member includes an actuator stop dimensioned to operatively engage the switch actuator to prevent movement of the switch actuator from the first longitudinal position to the second longitudinal position when the rotatable lock member is in the unlocked condition, and to permit movement of the switch actuator to the second longitudinal position when the rotatable lock member is rotated to the locked condition such that the switch plunger contacts and activates the electric switch. A loading unit is releasably couplable to the rotatable lock member and has an end effector dimensioned to perform a surgical procedure. The loading unit is secured relative to the elongate member when the rotatable lock member is in the locked condition.

In one aspect, the switch plunger is at least partially supported within a correspondingly dimensioned inner recess defined in the elongate member. The switch plunger is dimensioned to longitudinally traverse the recess during longitudinal movement of the switch actuator between the first and second longitudinal positions. The inner recess of the elongate member may be dimensioned to minimize lateral movement of the switch plunger during longitudinal movement of the switch actuator between the first and second longitudinal positions.

In embodiments, the activation link includes a mount tab which is received within a correspondingly dimensioned opening of the switch plunger to mechanically couple the activation link and the switch plunger. The mount tab may be dimensioned to permit lateral movement of the activation link relative to the mount tab when subjected to a lateral force during mounting and removal of the loading unit relative to the rotatable lock member.

In one aspect, the actuator stop includes a rod mounted to an external surface of the rotatable lock member. In an embodiment, the switch plunger includes a plunger extension which is engagable with the electric switch upon movement of the switch actuator to the second longitudinal position.

In embodiments, a controller is in electrical communication with the electric switch. The electric switch sends at least one electric signal to the controller to indicate that the loading unit is secured relative to the elongate member. The switch actuator may be normally biased toward the second longitudinal position. A spring may be engagable with the switch actuator to normally bias the switch actuator toward the second longitudinal position. The switch may include an outer elastic protective membrane.

In another aspect, a surgical apparatus includes a handle assembly and an adapter assembly couplable to the handle assembly. The adapter assembly includes an elongate member defining a longitudinal axis and having an inner recess, and a switch actuator. The switch actuator includes an activation link with a mount tab and a switch plunger with a correspondingly dimensioned opening for receiving the mount tab to mechanically couple the activation link and the switch plunger. The switch plunger is at least partially disposed within the inner recess of the elongate member. The switch actuator is adapted for longitudinal movement relative to the elongate member between first and second longitudinal positions of the switch actuator whereby the switch plunger traverses the inner recess of the elongate member. An electric switch is mounted to the elongate member in longitudinal alignment with the switch plunger. A rotatable lock member is mounted to the elongate member and adapted for rotational movement about the longitudinal axis between an unlocked condition and a locked condition. The rotatable lock member includes an actuator stop dimensioned to operatively engage the switch actuator to prevent movement of the switch actuator from the first longitudinal position to the second longitudinal position when the rotatable lock member is in the unlocked condition, and to permit movement of the switch actuator to the second longitudinal position when the rotatable lock member is rotated to the locked condition such that the switch plunger contacts and activates the electric switch. A loading unit is releasably couplable to the rotatable lock member and has an end effector dimensioned to perform a surgical procedure. A controller including logic is configured to receive a signal from the electric switch when the rotatable lock member is in the locked condition corresponding to a secured condition of the loading unit relative to the rotatable lock member and the adapter assembly.

In embodiments, the mount tab of the switch actuator is dimensioned to permit lateral movement of the activation link relative to the mount tab when subjected to a lateral force during mounting and removal of the loading unit relative to the rotatable lock member. In one aspect, the actuator stop includes a rod mounted to an external surface of the rotatable lock member. The inner recess of the elongate member may be dimensioned to minimize lateral movement of the switch plunger during longitudinal movement of the switch actuator between the first and second longitudinal positions. The switch plunger may include a plunger extension, which is engagable with the electric switch upon movement of the switch actuator to the second longitudinal position.

The activation mechanism of the surgical apparatus facilitates proper and repetitive placement of multiple loading units relative to a handle and/or adapter assembly without degrading the interconnecting components thereby extending life and usability of the assemblies and ensuring proper functioning thereof. Other advantages of the present disclosure will be appreciated from the following description.

BRIEF DESCRIPTION OF THE DRAWINGS

Embodiments of the present disclosure will be readily appreciated by reference to the drawings wherein:

FIG. 2 is a perspective view of the adapter assembly and the loading unit illustrating the activation mechanism for confirming mounting of the loading unit relative to the adapter assembly and the handle assembly;

FIG. 3 is a perspective view of the switch plunger of the activation mechanism;

FIG. 6 is a perspective view illustrating the loading unit mounted to the adapter assembly with the rotatable lock member in an unlocked condition and the switch actuator in a first longitudinal position;

FIG. 7 is an enlarged view of the area of isolation depicted in FIG. 2 illustrating the electric switch of the adapter assembly;

DETAILED DESCRIPTION OF EMBODIMENTS

Figure 1:
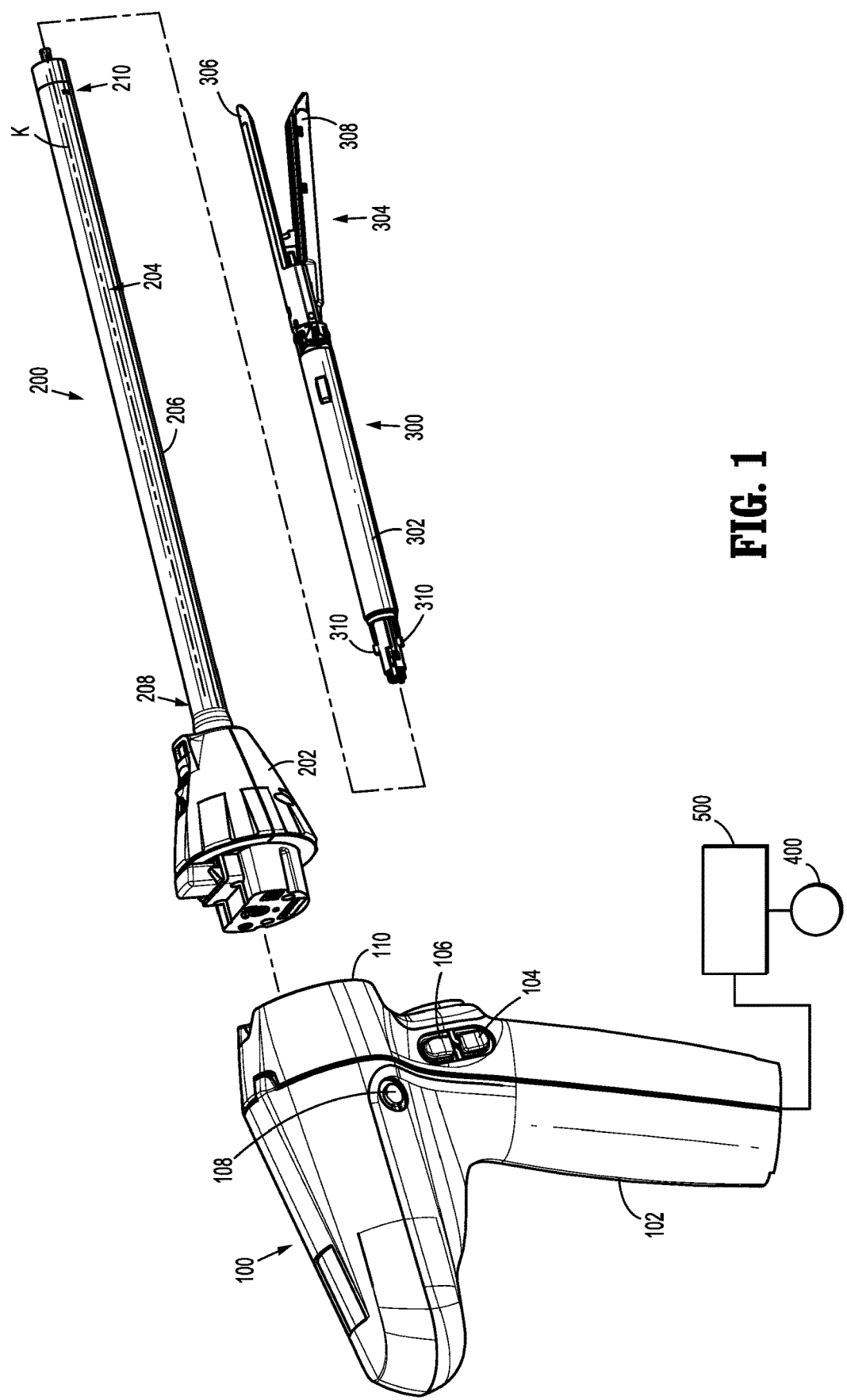
FIG. 1 is an exploded perspective view of a surgical fastener apparatus in accordance with the principles of the present disclosure, illustrating a handle assembly, an adapter assembly and a disposable loading unit.

Embodiments of the presently disclosed surgical apparatus, and adapter and handle assemblies for the surgical apparatus are described in detail with reference to the drawings, in which like reference numerals designate identical or corresponding elements in each of the several views. As used herein the term "distal" refers to that portion of the surgical apparatus, or component thereof, farther from the user, while the term "proximal" refers to that portion of the surgical apparatus, or component thereof, closer to the user.

Referring now to the drawings where like reference numerals indicate similar components throughout the several views, FIG. 1 illustrates the surgical fastener apparatus 10 in accordance with the principles of the present disclosure. The surgical fastener apparatus 10 includes a handle assembly 100, an adapter assembly 200 mountable to the handle assembly 100 and a loading unit 300 which is releasably couplable to the adapter assembly 200. The handle assembly 100 may be any handle assembly (reusable or disposable) having a handle frame 102 and at least one actuator, and in some embodiments, two or more actuators, control and/or safety switches 104, 106, 108 adapted to control operation of the fastener apparatus 10. The handle assembly 100 may be powered, e.g., an electromechanical handle, incorporating a motor 400 and a controller 500 having associated logic, software or circuitry to control operation of the motor 400, and, in turn, control operation of the adapter assembly 200 and the loading unit 300. The actuators 104, 106, 108 may communicate with the controller 500 to control operation of the motor 400 and the various pusher, gears, linkages and/or drive components within the handle frame 102. The handle frame 102 includes a handle mount 110 for mechanically mounting the adapter assembly 200 to the handle assembly 100. The handle mount 110 includes various circuits, contacts etc. to electrically communicate with various corresponding electrical components of the adapter assembly 200. Further details of a suitable handle for use with the fastener apparatus 10 may be ascertained by reference to commonly assigned U.S. Patent Publication No. 2011/0121049 to Malinouskas et al. or U.S. Patent Publication No. 2013/0214025 to Zemlok et al., the entire contents of each document being incorporated by reference herein.

The adapter assembly 200 is adapted to convert movement, e.g., rotation or linear movement, of the mechanical components of the handle assembly 100 to actuate the loading unit 300. The adapter assembly 200 includes an adapter mount 202 and an elongate member 204 extending from the adapter mount 202, and defining a longitudinal axis "k". The adapter mount 202 includes various contacts, switches or the like which communicate with cooperative components within the handle mount 110 of the handle assembly 100 when the adapter mount 202 is mounted to the handle mount 110 to control operation of the adapter assembly 200 and the loading unit 300. The elongate member 204 includes an outer tube 206 extending between proximal and distal ends 208, 210 of the elongate member 204. The outer tube 206 supports one or more drive mechanisms which control operation of the loading unit 300. Further details of the adapter assembly 200 will be discussed hereinbelow.

With continued reference to FIG. 1, the loading unit 300 may be a single use loading unit (SULU) adapted to perform a surgical procedure on tissue. It is also contemplated that the loading unit 300 may be a multi-use loading unit (MULU) adapted, e.g., for sequential firing of one or more fasteners or staples. In one embodiment, the loading unit 300 may be a SULU adapted to fire a linear array of fasteners in connection, e.g., a linear stapling procedure or anastomosis. In accordance with this embodiment, the loading unit 300 includes an elongated body 302 and an end effector or tool assembly 304 mounted at the end of the elongated body 302. The elongated body 302 is releasably mountable relative to the distal end 210 of the outer tube 206 of the adapter assembly 200. The end effector 304 includes an anvil 306 and a fastener cartridge 308. The fastener cartridge 308 houses at least one row, e.g., preferably a plurality of rows of fasteners or staples (not shown) each arranged in a linear array. The anvil 306 and the fastener cartridge 308 are adapted for relative movement between an open position (FIG. 1) and an approximated position. The fasteners are driven from the fastener cartridge 308 through tissue positioned about or between the components, and crimped by the anvil 306. As best depicted in FIG. 2, in conjunction with FIG. 1, the elongated body 302 further includes a pair of diametrically opposed mounting lugs 310 and a mounting fin 312 which mechanically couple with the adapter assembly 200. In addition, at least one, e.g., two electrical contacts 314 are mounted to the elongated body 302. The contacts 314 may be associated with, or in communication with a memory chip which stores parameters relating to the loading unit 300 such as serial number, type, size, staple or fastener size, length, maximum number of strokes, prior use of the loading unit, etc. Further details of the loading unit 300 may be ascertained by reference to commonly assigned U.S. patent application Ser. No. 14/863,558 to Zergiebel et al., filed Sep. 24, 2015, the entire contents of which are incorporated by reference herein.

Referring now to FIGS. 2-6, the activation mechanism of the adapter assembly 200 will now be discussed. The activation mechanism 212 provides positive feedback to the clinician that the loading unit 300 has been properly mounted to the adapter assembly 200, and in conjunction with memory or logic associated within the loading unit 300, provides information to the clinician regarding particulars (including, type, use, etc.) of the loading unit 300. The activation mechanism 212 also permits repetitive mounting of multiple loading units 300 without experiencing any degradation of its mechanical and/or electrical components within the adapter assembly 200 thereby enhancing usability and ensuring proper functioning of the adapter assembly 200 over an extended number of uses.

The activation mechanism 212 includes a switch actuator 214 which is mounted within the outer tube 206 (shown partially removed in FIG. 2) of the elongate member 204. In one embodiment, the switch actuator 214 is mounted relative to an inner housing 216 of the elongate member 204 and is adapted for longitudinal movement relative to the inner housing 216 between first and second longitudinal positions. FIG. 2 depicts the first or initial position of the switch actuator 214. The switch actuator 214 includes an activation link 218 and a switch plunger 220 coupled to the activation link 218. The activation link 218 includes a proximal mount segment 222 having a longitudinal slot 224 and a distal arm segment 226 depending from the proximal mount segment 222. The distal arm segment 226 has a generally elongated arm tip 230 depending therefrom. The distal arm segment 226 also defines a stop surface 232 (FIG. 5) adjacent the intersection of the arm tip 230 with the distal arm segment 226. A mount tab 234 projects radially outwardly from an intermediate segment of the activation link 218. The mount tab 234 defines a general rectangular cross-section and has a slightly curved or bowed profile.

With continued reference to FIGS. 2-6, the switch plunger 220 includes a plunger frame 236 defining a general rectangular opening 238 (FIGS. 3 and 5) therethrough for reception of the mount tab 234 of the activation link 218. In particular, the rectangular opening 238 of the switch plunger 220 and the rectangular cross-section of the mount tab 234 are correspondingly dimensioned whereby the mount tab 234 may be inserted within the rectangular opening 238 to couple the two components. The tolerance between the mount tab 234 and the opening 238 is selected such that the mount tab 234 may be capable of limited sliding movement in a direction transverse to the longitudinal axis "k" when mounted within the elongate member 204, e.g., in one embodiment, the mount tab 234 is not directly secured to the plunger frame 236 of the switch plunger 220. The switch plunger 220 includes a plunger extension or tab 240. The plunger frame 236 of the switch plunger 220 is at least partially received within a recess 242 (FIGS. 2 and 6) of the inner housing 216, and is adapted to traverse the recess 242 during longitudinal movement of the switch actuator 214 between first and second longitudinal positions. The recess 242 is correspondingly dimensioned to restrict lateral movement of the switch plunger 220. Specifically, the width "m" of the recess 242 (FIG. 6) generally corresponds to, e.g., is slightly greater than the width "b" of the plunger frame 236. (FIG. 3) With this dimensioning, the plunger frame 236 moves in a substantially direct linear manner while traversing the recess 242 with effectively no lateral movement.

As best depicted in FIGS. 2 and 6, the switch actuator 214 is normally biased in a distal direction, e.g., toward the second longitudinal position, by a resilient member or spring 244. The spring 244 engages, at its proximal end, a spring support wall 246 of the inner housing 216 of the elongate member 204 and, at its distal end, a spring bearing surface 248 of the activation link 218. The spring support wall 246 also extends within the longitudinal slot 224 of the activation link 218 and serves as a guide rail by traversing the longitudinal slot 224 thereby minimizing lateral movement of the switch actuator 214 during longitudinal movement between the first and second longitudinal positions.

Figure 4:
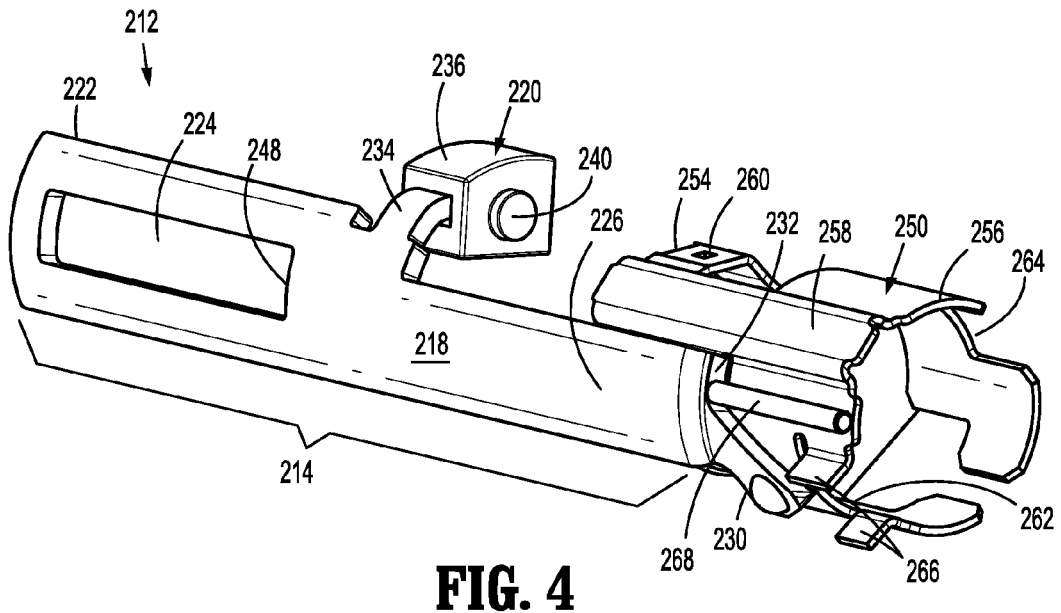
FIG. 4 is a perspective view of the activation mechanism illustrating the switch actuator and the rotatable lock member.
Figure 5:
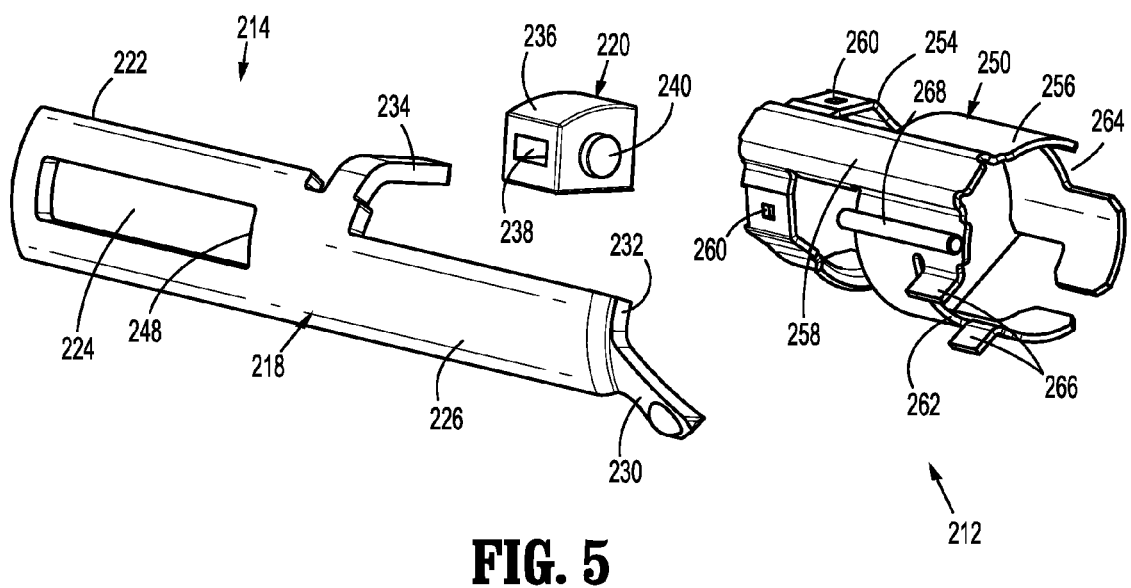
FIG. 5 is an exploded perspective view of the activation mechanism illustrating the activation link and the switch plunger of the switch actuator, and the rotatable lock member.

Referring now to FIGS. 4-5, in conjunction with FIG. 2, the activation mechanism 212 of the adapter assembly 200 further includes a rotatable lock member 250 at least partially mounted within a cap segment 252 (FIG. 2) disposed at the distal end 210 of the elongate member 204. The rotatable lock member 250 is adapted to rotate about the longitudinal axis "k" between two angular positions corresponding to the unlocked condition (FIG. 2) and the locked condition of the loading unit 300 relative to the adapter assembly 200. The rotatable lock member 250 includes first and second ring segments 254, 256 interconnected by a connecting arm 258. The first ring segment 254 includes at least one or more electrical contacts 260 which may communicate with the controller 500 to transfer data associated with the loading unit 300 when the loading unit 300 is mounted to the adapter assembly 200. The second ring segment 256 defines diametrically opposed recesses 262, 264 which couple with the loading unit 300. The recess 262 is defined between a pair of legs 266 depending outwardly from the second ring segment 256.

The second ring segment 256 further has an actuator stop 268 mounted to its external surface. The actuator stop 268 may be a cylindrical rod disposed in general longitudinal alignment with the switch actuator 214, particularly, the stop surface 232 of the activation link 218 when the rotatable lock member 250 is in the unlocked condition of FIG. 2. In this position, the stop surface 232 of the activation link 218 engages the actuator stop 268 to thereby prevent the switch actuator 214 from moving in a distal direction (in response to the spring bias of the spring 244) toward its second longitudinal position.

With reference again to FIGS. 2 and 6, further details of the adapter assembly 200 will be described. The adapter assembly 200 also includes an electric switch 270 which is mounted to the inner housing 216 of the elongate member 204 in general longitudinal alignment with the plunger extension 240 of the switch plunger 220. The switch 270 is configured to toggle, e.g., a toggle switch, in response to movement of the switch actuator 214, including the switch plunger 220, to the second longitudinal position, which occurs upon coupling of the loading unit 300 to the adapter assembly 200. The switch 270 is in electrical communication with the controller 500, and may include logic, circuitry or software to send one or more electrical signals to the controller 500 upon its activation and deactivation. As best depicted in FIG. 7, a switch seal or outer membrane 272 (portion of which is shown removed) may enclose the switch 270 to protect its components. The outer membrane 272 may be an elastomeric cover or the like. The switch 270 and the plunger extension 240 of the switch plunger 220 may have substantially the same cross-sectional areas "a1", "a2" (FIGS. 3 and 7) to ensure proper direct contact and activation of the plunger extension 240 with the switch 270.

The adapter assembly 200 further includes a drive member 274 extending through the outer tube 206 and beyond the cap segment 252. The drive member 274 is mechanically couplable to drive components of the handle assembly 100 upon coupling of the handle assembly 100 and the adapter assembly 200. A connector 276 is incorporated in the drive member 274, and is configured and dimensioned for selective engagement with associated drive mechanism(s) of the loading unit 300 to control operation of the loading unit 300.

Figure 8:
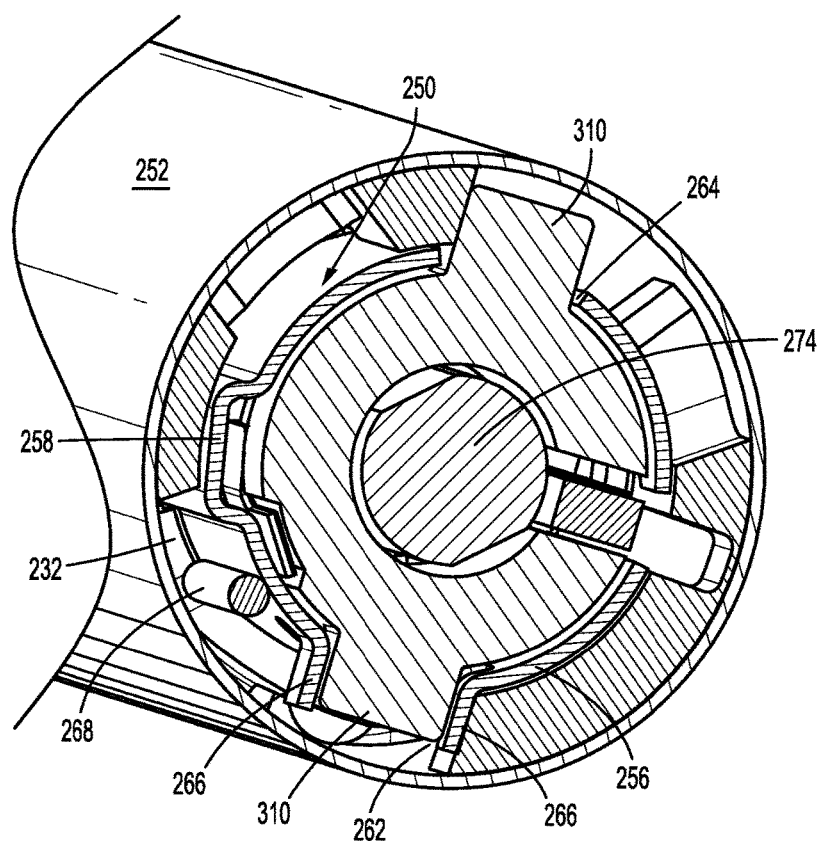
FIG. 8 is a perspective view in cross-section along the lines 8-8 of FIG. 6 illustrating the loading unit mounted to the adapter assembly with the rotatable lock member in the unlocked condition.

The operation of the activation mechanism 212 now will be discussed. The handle assembly 100 and the adapter assembly 200 are coupled by insertion of the adapter mount 202 of the adapter assembly 200 within the handle mount 110 of the handle assembly 100 (FIG. 1). Thereafter, the loading unit 300 is aligned with the cap segment 252 of the elongate member 204 of the adapter assembly 200 such that the mounting lugs 310 of the loading unit 300 are in alignment with the mounting recesses 262, 264 of the second ring segment 256 of the rotatable lock member 250 as depicted in FIG. 2. The loading unit 300 is introduced within the cap segment 252 whereby the mounting lugs 310 are received within the mounting recesses 262, 264 of the rotatable lock member 250 and the drive member 274 of the adapter assembly 200 is positioned within the loading unit 300 as depicted in FIGS. 6 and 8. The mounting fin 312 of the loading unit 300 is also accommodated within the underlying recess defined by the connecting arm 258. In this position, the actuator stop 268 of the rotatable lock member 250 engages the stop surface 232 of the activation link 218 in a manner to prevent the switch actuator 214 from moving in a distal direction toward the second longitudinal position. In one embodiment, the switch actuator 214 may be in the second longitudinal position such that during insertion of the loading unit 300 within the rotatable lock member 250 the actuator stop 268 may engage the stop surface 232 of the activation link 218 to move the switch actuator 214 to the first longitudinal position.

At this point in the procedure, the rotatable lock member 250 is in the unlocked condition relative to the mounting lugs 310 of the loading unit 300. The electrical contacts 314 of the loading unit 300 are in engagement with the electrical contacts 260 of the first ring segment 254 of the rotatable lock member 250. (FIG. 6)

Figure 9:
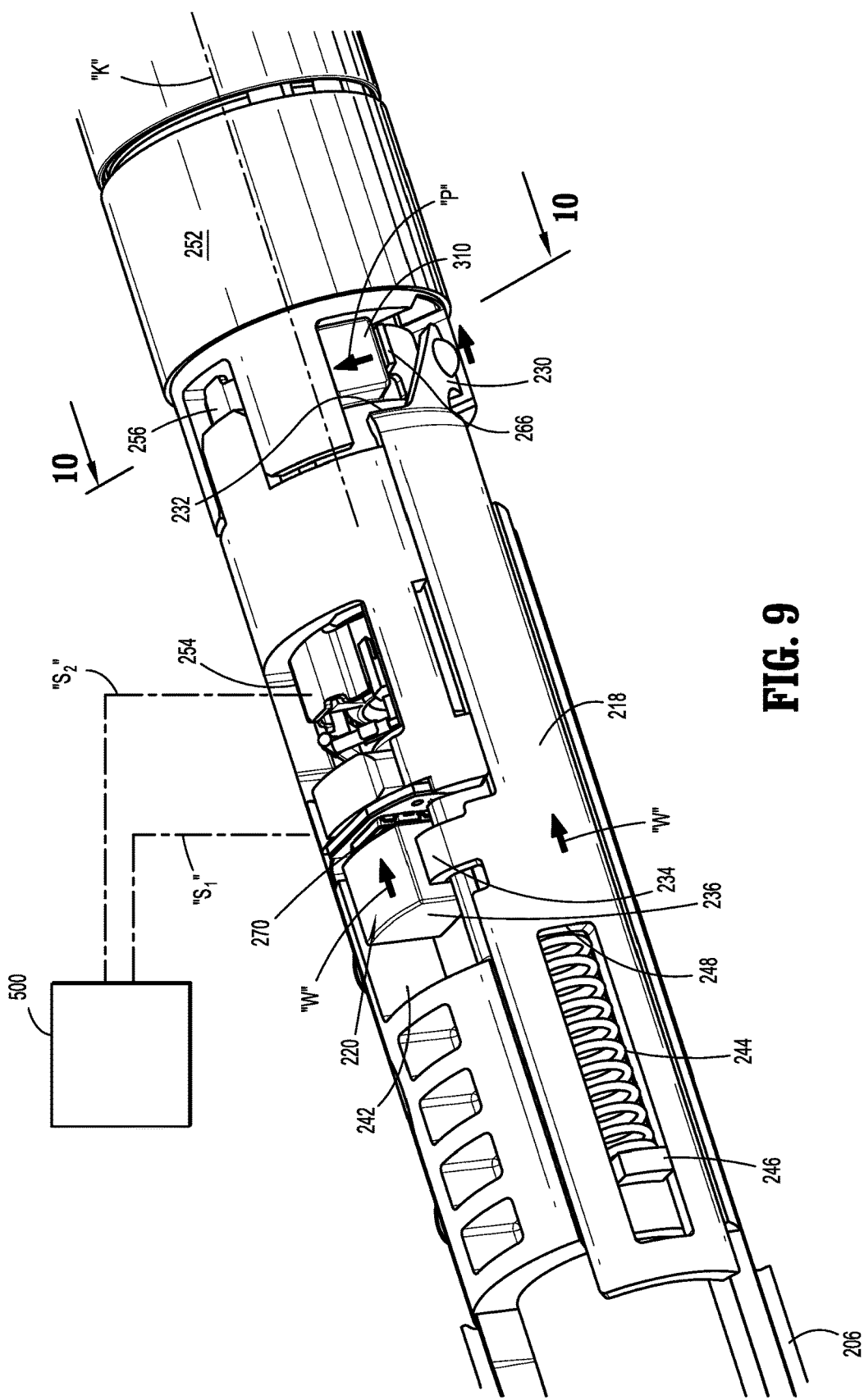
FIG. 9 is a perspective view similar to the view of FIG. 6 illustrating the rotatable lock member in the locked condition securing the loading unit and the switch actuator in the second longitudinal position in contact with the switch.
Figure 10:
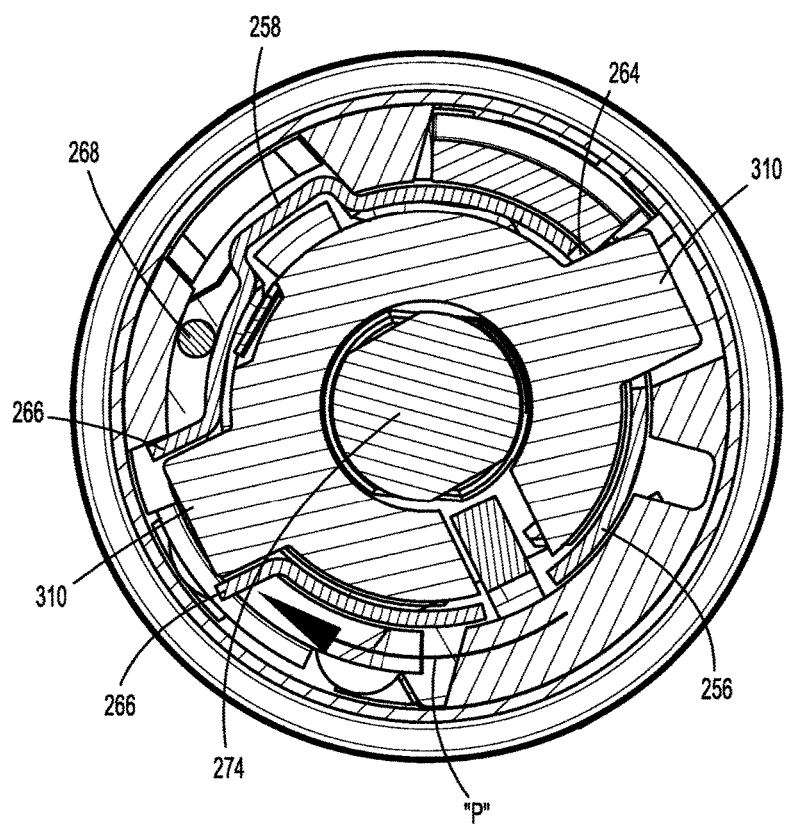
FIG. 10 is a cross-sectional view along the lines 10-10 of FIG. 9 illustrating the rotatable lock member in the locked condition.

With reference to FIGS. 9 and 10, the loading unit 300 is rotated (in the angular direction of directional arrow "p") about the longitudinal axis "k" to the locked condition, which causes the rotatable lock member 250 to correspondingly rotate due to engagement of the mounting lugs 310 of the loading unit 300 with the mounting recesses 262, 264 of the rotatable lock member 250 (e.g., with the legs 266 defining recess 262 and/or with the surfaces of the first ring segment 254 defining the recess 264). Upon rotation to the locked condition, the actuator stop 268 is displaced or moved out of longitudinal alignment with the activation link 218 thereby permitting the switch actuator 214 including the switch plunger 220 to advance in a distal longitudinal direction (directional arrow "w") to the second longitudinal position of FIG. 9 under the influence of spring 244. During this movement, the plunger frame 236 of the switch plunger 220 traverses the recess 242 of the inner housing 216 in direct linear manner such that the plunger extension 240 maintains longitudinal alignment with the switch 270. Due to the cooperative dimensioning of the recess 242 and the plunger frame 236, the switch 270 is not subjected to any off-axis forces which may affect the integrity of the switch seal or the outer membrane 272 and/or the switch components. In addition, during rotation, the activation link 218 of the switch actuator 214 may be permitted to move slightly laterally or outwardly due to the free coupling of the mount tab 234 of the activation link 218 within the opening 238 of the plunger frame 236, i.e., the mount tab 234 may slide to accommodate any radial outward or torque force to which the activation link 218 may be subjected during rotation of the rotatable lock member 250. This minimizes any off-axis or angular movement of the switch plunger 220 before and/or during traversing movement of the switch plunger 220 to maintain the integrity of the operative components and ensure direct contact of the plunger extension 240 with the switch 270. In the second longitudinal position, the plunger extension 240 of the switch actuator 214 engages and activates the switch 270 whereby the switch 270 sends a signal "s1" (shown schematically in FIG. 9) to the controller 500 that the loading unit 300 is engaged with the adapter assembly 200. The electrical contacts 314, 260 of the loading unit 300 and the rotatable lock member 250 send at least one signal "s2" (also shown schematically in FIG. 1) to transfer data associated with the loading unit 300 to the controller 500 for review by the clinician.

The above description and the drawings are provided for the purpose of describing embodiments of the present disclosure and are not intended to limit the scope of the disclosure in any way. It will be apparent to those skilled in the art that various modifications and variations can be made without departing from the spirit or scope of the disclosure. Thus, it is intended that the present disclosure cover the modifications and variations of this disclosure provided they come within the scope of the appended claims and their equivalents.

What is claimed is:

1. A surgical apparatus, which comprises:
   a handle;
   an elongate member coupled to the handle and defining a longitudinal axis, and having proximal and distal ends;
   a switch actuator mounted to the elongate member, the switch actuator adapted for longitudinal movement relative to the elongate member between first and second longitudinal positions, the switch actuator including an activation link and a switch plunger coupled to the activation link;
   an electric switch mounted to the elongate member in longitudinal alignment with the switch plunger;
   a rotatable lock member mounted to the elongate member and adapted for rotational movement about the longitudinal axis between an unlocked condition and a locked condition, the rotatable lock member including an actuator stop dimensioned to operatively engage the switch actuator to prevent movement of the switch actuator from the first longitudinal position to the second longitudinal position when the rotatable lock member is in the unlocked condition, and to permit movement of the switch actuator to the second longitudinal position when the rotatable lock member is rotated to the locked condition such that the switch plunger contacts and activates the electric switch; and
   a loading unit releasably couplable to the rotatable lock member and having an end effector dimensioned to perform a surgical procedure, the loading unit being secured relative to the elongate member when the rotatable lock member is in the locked condition.

2. The surgical apparatus according to claim 1 wherein the switch plunger is at least partially supported within a correspondingly dimensioned inner recess defined in the elongate member, the switch plunger dimensioned to longitudinally traverse the recess during longitudinal movement of the switch actuator between the first and second longitudinal positions.

3. The surgical apparatus according to claim 2 wherein the inner recess of the elongate member is dimensioned to minimize lateral movement of the switch plunger during longitudinal movement of the switch actuator between the first and second longitudinal positions.

4. The surgical apparatus according to claim 1 wherein the activation link includes a mount tab, the mount tab received within a correspondingly dimensioned opening of the switch plunger to mechanically couple the activation link and the switch plunger.

5. The surgical apparatus according to claim 4 wherein the mount tab is dimensioned to permit lateral movement of the activation link relative to the mount tab when subjected to a lateral force during mounting and removal of the loading unit relative to the rotatable lock member.

6. The surgical apparatus according to claim 1 wherein the actuator stop includes a rod mounted to an external surface of the rotatable lock member.

7. The surgical apparatus according to claim 1 wherein the switch plunger including a plunger extension, the plunger extension engagable with the electric switch upon movement of the switch actuator to the second longitudinal position.

8. The surgical apparatus according to claim 7 including a controller in electrical communication with the electric switch, the electric switch sending at least one electric signal to the controller to indicate that the loading unit is secured relative to the elongate member.

9. The surgical apparatus according to claim 1 wherein the switch actuator is normally biased toward the second longitudinal position.

10. The surgical apparatus according to claim 9 including a spring engagable with the switch actuator to normally bias the switch actuator toward the second longitudinal position.

11. The surgical apparatus according to claim 1 wherein the switch includes an outer elastic protective membrane.

12. A surgical apparatus, which comprises:
    a handle assembly;
    an adapter assembly couplable to the handle assembly, the adapter assembly including:
       an elongate member defining a longitudinal axis, and having proximal and distal ends, and defining an inner recess;
       a switch actuator including an activation link having a mount tab and a switch plunger having a correspondingly dimensioned opening for receiving the mount tab to mechanically couple the activation link and the switch plunger, the switch plunger at least partially disposed within the inner recess of the elongate member, the switch actuator adapted for longitudinal movement relative to the elongate member between first and second longitudinal positions of the switch actuator whereby the switch plunger traverses the inner recess of the elongate member;
       an electric switch mounted to the elongate member in longitudinal alignment with the switch plunger; and
       a rotatable lock member mounted to the elongate member and adapted for rotational movement about the longitudinal axis between an unlocked condition and a locked condition, the rotatable lock member including an actuator stop dimensioned to operatively engage the switch actuator to prevent movement of the switch actuator from the first longitudinal position to the second longitudinal position when the rotatable lock member is in the unlocked condition, and to permit movement of the switch actuator to the second longitudinal position when the rotatable lock member is rotated to the locked condition such that the switch plunger contacts and activates the electric switch;
    a loading unit releasably couplable to the rotatable lock member and having an end effector dimensioned to perform a surgical procedure; and
    a controller including logic configured to receive a signal from the electric switch when the rotatable lock member is in the locked condition corresponding to a secured condition of the loading unit relative to the rotatable lock member and the adapter assembly.

13. The surgical apparatus according to claim 12 wherein the mount tab is dimensioned to permit lateral movement of the activation link relative to the mount tab when subjected to a lateral force during mounting and removal of the loading unit relative to the rotatable lock member.

14. The surgical apparatus according to claim 13 wherein the actuator stop includes a rod mounted to an external surface of the rotatable lock member.

15. The surgical apparatus according to claim 12 wherein the inner recess of the elongate member is dimensioned to minimize lateral movement of the switch plunger during longitudinal movement of the switch actuator between the first and second longitudinal positions.

16. The surgical apparatus according to claim 12 wherein the switch plunger including a plunger extension, the plunger extension engagable with the electric switch upon movement of the switch actuator to the second longitudinal position.

\* \* \* \* \*